United States Patent
Lebaut et al.

(10) Patent No.: US 6,919,344 B2
(45) Date of Patent: Jul. 19, 2005

(54) N-SUBSTITUTED INDOLE-3-GLYOXYLAMIDES HAVING ANTI-ASTHMATIC, ANTIALLERGIC AND IMMUNOSUPPRESSANT/IMMUNO-MODULATING ACTION

(75) Inventors: Guillaume Lebaut, Saint Sebastien/Loire (FR); Cécilia Menciu, Nantes (FR); Bernhard Kutscher, Maintal (DE); Peter Emig, Bruchköbel (DE); Stefan Szelenyi, Schwaig (DE); Kay Brune, Marloffstein/Rathsberg (DE)

(73) Assignee: ASTA MEDICA, Aktiengesellschaft, Dresden (DE)

( * ) Notice: Subject to any disclaimer, the term of this patent is extended or adjusted under 35 U.S.C. 154(b) by 39 days.

(21) Appl. No.: 10/402,931

(22) Filed: Apr. 1, 2003

(65) Prior Publication Data

US 2003/0207892 A1 Nov. 6, 2003

Related U.S. Application Data

(60) Continuation of application No. 10/058,836, filed on Jan. 30, 2002, now abandoned, which is a division of application No. 09/409,263, filed on Sep. 30, 1999, now Pat. No. 6,344,467, which is a division of application No. 08/925,326, filed on Sep. 8, 1997, now Pat. No. 6,008,231.

(30) Foreign Application Priority Data

Sep. 6, 1996 (DE) .......................... 196 36 150

(51) Int. Cl.$^7$ ..................... A61K 31/404; A61K 31/496; A61K 31/506
(52) U.S. Cl. ....................... 514/256; 514/323; 514/339; 514/419
(58) Field of Search ................. 514/256, 323, 514/339, 419

(56) References Cited

U.S. PATENT DOCUMENTS

| | | | | |
|---|---|---|---|---|
| 6,008,231 A | * | 12/1999 | Lebaut et al. | 514/314 |
| 6,344,467 B1 | * | 2/2002 | Lebaut et al. | 514/339 |
| 2004/0171668 A1 | * | 9/2004 | Nickel et al. | 514/414 |
| 2004/0266762 A1 | * | 12/2004 | Gerlach | 514/227.5 |

* cited by examiner

*Primary Examiner*—Fiona T. Powers
(74) *Attorney, Agent, or Firm*—Pillsbury Winthrop Shaw Pittman, LLP

(57) ABSTRACT

The invention relates to novel N-substituted indole-3-glyoxylamides, to processes for their preparation and to their pharmaceutical use. The compounds have antiasthmatic, antiallergic and immuno-suppressant/immunomodulating actions.

10 Claims, No Drawings

N-SUBSTITUTED INDOLE-3-GLYOXYLAMIDES HAVING ANTI-ASTHMATIC, ANTIALLERGIC AND IMMUNOSUPPRESSANT/IMMUNO-MODULATING ACTION

CROSS-REFERENCE TO RELATED APPLICATIONS

This is a continuation of U.S. patent application Ser. No. 10/058,836, filed Jan. 30, 2002 now abandoned, which is a divisional of U.S. patent application Ser. No. 09/409,263, filed Sep. 30, 1999, now U.S. Pat. No. 6,344,467, which in turn is a divisional of U.S. patent application Ser. No. 08/925,326, filed Sep. 8, 1997, now U.S. Pat. No. 6,008,231 and claims priority to German Patent Application No. 196 36 150.8, filed Sep. 6, 1996.

FIELD OF THE INVENTION

The filed of the invention is directed to N-substituted indole-3-glyoxylamides having anti-asthmatic, antiallergic, and inununosuppressant/immuno-modulating action.

DESCRIPTION

Indole-3-glyoxylamides have various uses as pharmacodynamically active compounds and as synthesis components in the pharmaceutical chemistry.

The Patent Application NL 6502481 describes compounds which have an antiinflammatory and antipyretic profile of action and analgesic activity.

The British Patent GB 1 028 812 mentions derivatives of indolyl-3-glyoxylic acid and its amides as compounds having analgesic, anticonvulsant and β-adrenergic activity.

G. Domschke et al. (Ber. 94, 2353 (1961)) describe 3-indolylglyoxylamides which are not characterized pharmacologically.

E. Walton et al. in J. Med. Chem. 11,1252 (1968) report on indolyl-3-glyoxylic acid derivatives which have an inhibitory activity on glycerophosphate dehydrogenase and lactate dehydrogenase.

Euoropean Patent Specification EP 0 675 110 A1 describes 1H-indole-3-glyoxylamides which are profiled as sPLA2 inhibitors and are used in the treatment of septic shock, in pancreatitis, and in the treatment of allergic rhinitis and rheumatoid arthritis.

The aim of the present invention is to make available novel compounds from the indolyl-3-glyoxylic acid series, which have antiasthmatic and immunomodulating action.

The chemical processes for the preparation of these compounds and pharmaceutical processes for the conversion of the novel compounds into medicaments and their preparation forms are furthermore described.

The subject matter of the invention comprises compounds of the general formula I,

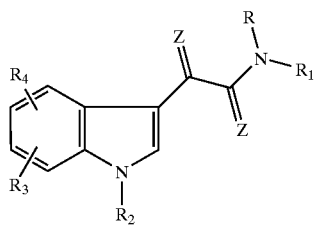

Formula I where the radicals R, $R_1$, $R_2$, $R_3$, $R_4$ and Z have the following meaning:

R=hydrogen, $(C_1-C_6)$-alkyl, where the alkyl group can be mono- or polysubstituted by the phenyl ring. This phenyl ring, for its part, can be mono- or polysubstituted by halogen, $(C_1-C_6)$-alkyl, $(C_3-C_7)$-cycloalkyl, by carboxyl groups, carboxyl groups esterified with $(C_1-C_6)$-alkanols, trifluoromethyl groups, hydroxyl groups, methoxy groups, ethoxy groups, benzyloxy groups and by a benzyl group which is mono- or polysubstituted in the phenyl moiety by $(C_1-C_6)$-alkyl groups halogen atoms or trifluoromethyl groups.

$R_1$ can be a phenyl ring which is mono- or polysubstituted by $(C_1-C_6)$-alkyl, $(C_1-C_6)$-alkoxy, hydroxyl, benzyloxy, nitro, amino, $(C_1-C_6)$-alkylamino, $(C_1-C_6)$-alkoxy-carbonylamino and by a carboxyl group or a carboxyl group esterified by $(C_1-C_6)$-alkanols, or is a pyridin structure of the formula II

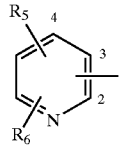

Formula II where the pyridin structure is alternatively bonded to the ring carbon atoms 2, 3 and 4 and can be substituted by the substitutents $R_5$ and $R_6$. The radicals $R_5$ and $R_6$ can be identical or different and have the meaning $(C_1-C_6)$-alkyl, and also the meaning $(C_3-C_7)$-cycloalkyl, $(C_1-C_6)$-alkoxy, nitro, amino, hydroxyl, halogen and trifluoromethyl and are furthermore the ethoxy-carbonylamino radical and the group carboxy-alkyloxy in which the alkyl group can have 1–4 C atoms.

$R_1$ can furthermore be a 2- or 4-pyrimidinyl-heterocycle or a pyridylmethyl radical in which $CH_2$ can be in the 2-, 3-, 4-position where the 2-pyrimidinyl ring can be mono- or polysubstituted by the methyl group, furthermore are [sic] the 2-, 3- and 4-quinolyl structure substituted by $(C_1-C_6)$-alkyl, halogen, the nitro group, the amino group and the $(C_1-C_6)$-alkylamino radical, or are [sic] a 2-, 3- and 4-quinolylmethyl group, where the ring carbons of the pyridylmethyl and quinolylmethyl radical can be substituted by $(C_1-C_6)$-alkyl, $(C_1-C_6)$-alkoxy, nitro, amino and $(C_1-C_6)$-alkoxy-carbonylamino.

$R_1$ for the case where R is hydrogen or the benzyl group, can furthermore be the acid radical of a natural or unnatural amino acid, e.g. the α-glycyl, the α-sarcosyl, the α-alanyl, the α-leucyl, the α-isoleucyl, the α-seryl, the α-phenylalanyl, the α-histidyl, the α-prolyl, the α-arginyl, the α-lysyl, the α-asparagyl and the α-glutamyl radical, where the amino groups of the respective amino acids can be present in unprotected or protected form. Possible protective groups for the amino function are the carbobenzoxy radical (Z radical) and the tert-butoxycarbonyl radical (BOC radical) and also the acetyl group. In the case of the asparagyl and glutamyl radical claimed for $R_1$, the second, nonbonded carboxyl group is present as a free carboxyl group or in the form of an ester with $C_1$–$C_6$-alkanols, e.g. as the methyl, ethyl or as the tert-butyl ester. $R_1$ can furthermore be the allylaminocarbonyl-2-methylprop-1-yl group. R and $R_1$, together with the nitrogen atom to which they are bonded, can furthermore form a piperazine ring of the formula III or a homopiperazine ring if $R_1$ is an aminoalkylene group in which Formula III

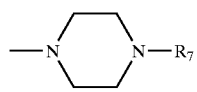

$R_7$ is an alkyl radical, a phenyl ring which can be mono- or polysubstituted by $(C_1$–$C_6)$-alkyl, $(C_1$–$C_6)$-alkoxy, halogen, the nitro group, the amino function, by $(C_1$–$C_6)$-alkylamino, the benzhydryl group and the bis-p-fluorobenzylhydryl group.

$R_2$ can be hydrogen or the $(C_1$–$C_6)$-alkyl group, where the alkyl group can be mono- or polysubstituted by halogen and phenyl which for its part can be mono- or polysubstituted by halogen, $(C_1$–$C_6)$-alkyl, $(C_3$–$C_7)$-cycloalkyl, carboxyl groups, carboxyl groups esterified with $(C_1$–$C_6)$-alkanols, trifluoromethyl groups, hydroxyl groups, methoxy groups, ethoxy groups or benzyloxy groups. The $(C_1$–$C_6)$-alkyl group counting as $R_2$ can furthermore be substituted by the 2-quinolyl group and the 2-, 3- and 4-pyridyl structure, which in each case can both be mono- or polysubstituted by halogen, $(C_1$–$C_4)$-alkyl groups or $(C_1$–$C_4)$-alkoxy groups. $R_2$ is furthermore the aroyl radical, where the aroyl moiety on which this radical is based is the phenyl ring which can be mono- or polysubstituted by halogen $(C_1$–$C_6)$-alkyl, $(C_3$–$C_7)$-cycloalkyl, carboxyl groups, carboxyl groups esterified by $(C_1$–$C_6)$-alkanols, trifluoromethyl groups, hydroxyl groups, methoxy groups, ethoxy groups or benzyloxy groups.

$R_3$ and $R_4$ can be identical or different and are hydrogen, hydroxyl, $(C_1$–$C_6)$-alkyl, $(C_3$–$C_7)$-cycloalkyl, $(C_1$–$C_6)$-alkanoyl, $(C_1$–$C_6)$-alkoxy, halogen and benzyloxy. $R_3$ and $R_4$ can furthermore be the nitro group, the amino group, the $(C_1$–$C_4)$-mono- or dialkyl-substituted amino group, and the $(C_1$–$C_3)$-alkoxycarbonylamino function or $(C_1$–$C_3)$-alkcoxy-carbonylamino-$(C_1$–$C_3)$-alkyl function.

Z is O or S

The designation alkyl, alkanol, alkoxy or alkylamino group for the radicals R, $R_1$, $R_2$, $R_3$, $R_4$, $R_5$, $R_6$ and $R_7$ is normally to be understood as meaning "straight-chain" and "branched" alkyl groups, where "straight-chain alkyl groups" can be, for example, radicals such as methyl, ethyl, n-propyl, n-butyl, n-pentyl and n-hexyl and "branched alkyl groups" designate, for example, radicals such as isopropyl or tert-butyl. "Cycloalkyl" is to be understood as meaning radicals such as, for example, cyclopropyl, cyclobutyl, cyclopentyl, cyclohexyl or cycloheptyl.

The designation "halogen" represents fluorine, chlorine, bromine or iodine. The designation "alkoxy group" represents radicals such as, for example, methoxy, ethoxy, propoxy, butoxy, isopropoxy, isobutoxy or pentoxy.

The compounds according to the invention can also be present as acid addition salts, for example as salts of mineral acids, such as, for example, hydrochloric acid, sulfuric acid, phosphoric acid, salts of organic acids, such as, for example, acetic acid, lactic acid, malonic acid, maleic acid, fumaric acid, gluconic acid, glucuronic acid, citric acid, embonic acid, methanesulfonic acid, trifluoroacetic acid and succinic acid.

Both the compounds of the formula I and their salts are biologically active. The compounds of the formula 1 can be administered in free form or as salts with a physiologically tolerable acid.

Administration can be carried out orally, parenterally, intravenously, transdermally or by inhalation.

The invention furthermore relates to pharmaceutical preparations containing at least one compound of the formula I or its salt with physiologically tolerable inorganic or organic acids and, if appropriate, pharmaceutically utilizable excipients and/or diluents or auxiliaries.

Suitable administration forms are, for example, tablets, coated tablets, capsules, solutions or ampoules, suppositories, patches, powder preparations which can be inhaled, suspensions, creams and ointments.

The compounds according to the invention have a good antiasthmatic, antiallergic and immunosuppressant/immunomodulating action, for example in transplantations and diseases such as psoriasis, rheumatoid disorders and chronic polyarthritis, in the following pharmacological models:

Inhibition of the "Late Phase" eosinophilia in the BAL 24 Hours after Allergen Challenge in Guinea Pigs Male guinea pigs (200–250 g, Dunkin Hartley Shoe) were actively sensitized subcutaneously with ovalbumin (10 µg of ovalbumin+1 mg of $Al(OH)_3$) and boosted 2 weeks later. One week after boosting with ovalbumin, the animals were exposed to an inhalation challenge with ovalbumin (0.5% strength solution) for 20–30 seconds. 24 hours later, the animals were killed by means of an overdose of urethane, exsanguinated and a bronchoalveolar lavage (BAL) was carried out using 2×5 ml of 0.9% strength physiological saline solution.

The lavage fluid was collected and centrifuged at 400 g for 10 minutes, and the pellets were suspended in 1 ml of 0.9% strength physiological saline solution. The eosinophils were counted microscopically in a Neubauer chamber after staining by means of Becton Dickinson test kit No. 5877. This test kit contains Phloxin B as a selective stain for eosinophils. The eosinophils in the BAL was [sic] counted here for each animal and expressed as eosinophils (millions/animal). For each group the mean value and standard deviation were determined. The percentage inhibition of eosinophilia for the group treated with test substance was calculated according to the following formula:

$(A-B)-(B-C)/(A-C)\times 100 = \%$ inhibition in this formula A eosinophils correspond to the untreated challenge group, B eosinophils to the treated group and C eosinophils to the unchallenged control group.

The animals were treated with a histamine $H_1$ antagonist (azelastine; 0.01 mg/kg p.o.) 2 hours before allergen challenge to avoid death. The administration of the test substances or of the vehicle was carried out 4 hours after allergen challenge. The percentage inhibition of eosinophilia in the BAL was calculated on groups of 6–10 animals.

TABLE

| | Inhibition of the "late phase" - eosinophilia 24 h after allergen challenge in guinea pigs | | | |
|---|---|---|---|---|
| Substance | Dose [mg/kg] | Administration | n | % Inhibition |
| Cyclosporin A | 5 | i.p. + 4 h | 17 | 50.0 |
| | 10 | i.p. + 4 h | 11 | 47.0 |
| | 30 | p.o. + 4 h | 10 | 68.8 |
| According to Ex. 1 | 5 | i.p. + 4 h | 10 | 27.8 |
| | 10 | i.p. + 4 h | 10 | 55.4 |
| | 30 | p.o. + 4 h | 9 | 56.1 |

Assays for the Determination of Peptidylprolyl Isomerase (PPIase) Activity and Inhibition The PPIase activity of the cyclophilins was measured enzymatically according to Fischer et al. (1984). After isomerization of the substrate by the peptidyl prolyl isomerase, this is accessible to chymotrypsin, which cleaves the chromophore p-nitroaniline. For the determination of inhibition of the PPIase activity by substance, recombinant human Cyp B was used. The interaction of Cyp B with a potential inhibitor was carried out as follows:

A certain concentration of purified Cyp B was incubated with 1 $\mu$M substance for 15 min. The PPIase reaction was started by addition of the substrate solution to the reaction mixture which contains HEPES buffer, chymotrypsin and either test or control samples. Under these conditions, first-order kinetics were obtained with a constant $K_{observed} = K_0 + K_{enz}$, where $K_0$ is the spontaneous isomerization and $K_{enz}$ is the rate of isomerization of the PPIase activity. The extinction values which correspond to the amount of the chromophore cleaved were measured using a Beckman DU 70 spectrophotometer at a constant reaction temperature of 10° C.

The observed residual activity in the presence of various substances was compared with the cyclophilins only treated with solvent. The results were given in % residual activity. Cyclosporin A (CsA) was used as the reference compound. The inhibition of the PPIase activity was additionally checked by SDS-PAGE.

Colorimetric Assay (Based on the MTT Test) for the Non-Radioactive Quantification of Cell Proliferation and Survival Ability MTT is used for the quantitative determination of cell proliferation and activation, for example, in the reaction on growth factors and cytokines such as IL-2 and IL-4 and also for the quantification of the antiproliferative or toxic effects.

The assay is based on the cleavage of yellow tetrazolium salt MTT to give purple-red formazan crystals by metabolically active cells.

The cells, cultured in a 96-hole tissue culture plate, are incubated for about 4 h with yellow MTT solution. After this incubation time, purple-red formazan salt crystals are formed. These salt crystals are insoluble in aqueous solutions, but can be dissolved by addition of solubilizer and by incubation of the plates overnight.

The dissolved formazan product is quantified spectrophotometrically using an ELISA reader. An increase in the number of living cells results in an increase in the total metabolic activity in the sample. This increase correlates directly with the amount of the purple-red formazan crystals formed, which are [sic] measured by the absorption.

| Substance | Inhibition of PPIase activity [%] | Inhibition of CD3-induced IL-2 production [%] | | | Inhibition of lympho-proliferation [%] | | |
|---|---|---|---|---|---|---|---|
| Conc. [$\mu$M] | | 0.1 | 1 | 10 | 0.1 | 1 | 10 |
| According to Ex. 1 | 80–100 | 34 | 72 | 95 | 18 | 39 | 61 |
| Cyclosporin A | 80–100 | 56 | 82 | 94 | 8 | 7 | 11 |

The processes for the preparation of the compounds according to the invention are described in the following reaction schemes 1 and 2 and in general procedures. All compounds can be prepared as described or analogously.

The compounds of the general formula I are obtainable according to the following Scheme 1, shown for the synthesis of the compound Example 1:

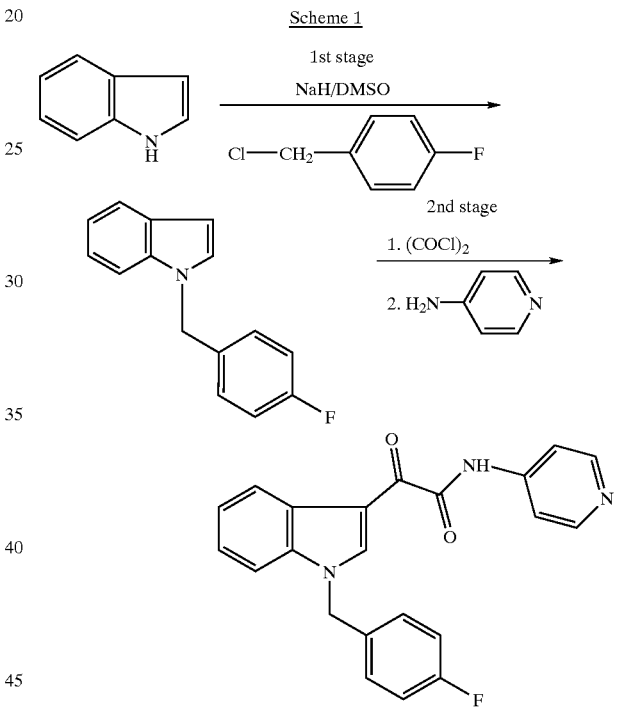

Scheme 1

General Procedure for the Preparation of the Compounds of the General Formula I According to Scheme 1:

1st Stage:

The indole derivative, which can be unsubstituted or mono- or polysubstituted on C-2 or in the phenyl structure, is dissolved in a protic, dipolar aprotic or nonpolar organic solvent, such as, for example, isopropanol, tetrahydrofuran, dimethyl sulfoxide, dimethylformamide, dimethylacetamide, N-methyl-pyrrolidone, dioxane, toluene or methylene chloride and added dropwise to a suspension of a base in a molar or excess amount prepared in a 3-necked flask under an $N_2$ atmosphere, such as, for example, sodium hydride, powdered potassium hydroxide, potassium tert-butoxide, dimethylaminopyridine or sodium amide in a suitable solvent. The desired alkyl, aralkyl or heteroaralkyl halide, if appropriate with addition of a catalyst, such as, for example, copper, is then added and the mixture is reacted for some time, for example 30 minutes to 12 hours, and the temperature is kept within a range from 0° C. to 120° C., preferably between 30° C. to [sic] 80° C., particularly between 50° C. and 65° C. After completion of the reaction, the reaction mixture is added to water, the solution is extracted, for example, with diethyl ether, dichloromethane, chloroform, methyl tert-butyl ether or tetrahydrofuran and the organic phase obtained in each case is dried using anhydrous sodium sulfate. The organic phase is concentrated in vacuo, the residue which remains is crystallized by trituration or the oily residue is purified by recrystallization, distillation or by column or flash chromatography on silica gel or alumina. The eluent used is, for example, a mixture of dichloromethane and diethyl ether in the ratio 8:2 (vol/vol) or a mixture of dichloromethane and ethanol in the ratio 9:1 (vol/vol).

2nd Stage

The N-substituted indole obtained by the abovementioned 1st stage procedure is dissolved under a nitrogen atmosphere in an aprotic or nonpolar organic solvent, such as, for example, diethyl ether, methyl tert-butyl ether, tetrahydrofuran, dioxane, toluene, xylene, methylene chloride or chloroform and added to a solution, prepared under a nitrogen atmosphere, of a simply molar up to 60 percent excess amount of oxalyl chloride in an aprotic or nonpolar solvent, such as, for example, in diethyl ether, methyl tert-butyl ether, tetrahydrofuran, dioxane, toluene, xylene, methylene chloride or chloroform, the temperature being kept between –5° C. and 20° C. The reaction solution is then heated at a temperature between 10° C. and 130° C., preferably between 20° C. and 80° C., particularly between 30° C. and 50° C., for a period of 30 minutes up to 5 hours and the solvent is then evaporated. The residue of the "indolyl-3-glyoxylic acid chloride" formed in this manner which remains is dissolved in an aprotic solvent such as, for example, tetrahydrofuran, dioxane, diethyl ether, toluene or alternatively in a dipolar aprotic solvent, such as, for example, dimethylformamide, dimethylacetamide or dimethyl sulfoxide, cooled to a temperature between 10° C. and –15° C., preferably between –5° C. and 0° C., and treated in the presence of an acid scavenger with a solution of the primary or secondary amine in a diluent.

Possible diluents are the solvents used above for the dissolution of the indolyl-3-glyoxylic acid chloride. Acid scavengers used are triethylamine, pyridin, dimethylaminopyridine, basic ion exchanger, sodium carbonate, potassium carbonate, powdered potassium hydroxide and excess primary or secondary amine employed for the reaction. The reaction takes place at a temperature from 0° C. to 120° C., preferably at 20–80° C., particularly between 40° C. and 60° C. After a reaction time of 1–3 hours and standing at room temperature for 24 hours, the hydrochloride of the acid scavenger is filtered, the filtrate is concentrated in vacuo, and the residue is recrystallized from an organic solvent or purified by column chromatography on silica gel or alumina. The eluent used is, for example, a mixture of dichloromethane and ethanol (95:5, vol/vol).

WORKING EXAMPLES

According to this general procedure for Stages 1 and 2, on which the synthesis Scheme 1 is based, the following compounds were synthesized which are evident from the following survey detailing the respective chemical name. In Table 1 which follows, the structures of these compounds and their melting points can be seen from the general formula I and the substituents $R_1$–$R_4$ and Z:

Example 1

N-(Pyridin-4-yl)-[1-(4-fluorobenzyl)indol-3-yl] glyoxylamide

1st Stage 1-(4-Fluorobenzyl)indole

A solution of 11.72 g (0.1 mol) of indole in 50 ml of dimethyl sulfoxide is added to a mixture of 2.64 g of sodium hydride (0.11 mol, mineral oil suspension) in 100 ml of dimethyl sulfoxide. The mixture is heated for 1.5 hours at 60° C., then allowed to cool and 15.9 g (0.11 mol) of 4-fluorobenzyl chloride are added dropwise. The solution is warmed to 60° C., allowed to stand overnight and then poured into 400 ml of water with stirring. The mixture is extracted several times with a total of 150 ml of methylene chloride, the organic phase is dried using anhydrous sodium sulfate and filtered, and the filtrate is concentrated in vacuo. The residue is distilled in a high vacuum:

21.0 g (96% of theory)

B.p. (0.5 mm): 140° C.

2nd Stage

N-(pyridin-4-yl)-[1-(4-fluorobenzyl)indol-3-yl] glyoxylamide

A solution of 4.75 g (21.1 mmol) of 1-(4-fluoro-benzyl)indole in 25 ml of ether is added dropwise at 0° C. and under $N_2$ to a solution of 2.25 ml of oxalyl chloride in 25 ml of ether. The mixture is refluxed for 2 hours and the solvent is then evaporated. 50 ml of tetrahydrofuran were [sic] then added to the residue, and the solution is cooled to –5° C. and treated dropwise with a solution of 4.66 g (49.5 mmol) of 4-aminopyridine in 200 ml of THF. The mixture is refluxed for 3 hours and allowed to stand at room temperature overnight. The 4-aminopyridine hydrochloride is filtered off with suction, the precipitate is washed with THF, the filtrate is concentrated in vacuo and the residue is recrystallized from ethyl acetate.

Yield: 7.09 g (90% of theory)

Melting point: 225–226° C.

| Elemental analysis: | | | | | | |
|---|---|---|---|---|---|---|
| Calc. | C | 70.77 | H | 4.32 | N | 11.25 |
| Found | C | 71.09 | H | 4.36 | N | 11.26 |
| Example 2 | | N-(Pyridin-4-yl)-(1-methylindol-3-yl) glyoxylamide | | | | |
| Example 3 | | N-(Pyridin-3-yl)-[1-(4-fluorobenzyl)-indol-3-yl]glyoxylamide | | | | |
| Example 4 | | N-(Pyridin-3-yl)-(1-benzylindol-3-yl) glyoxylamide | | | | |
| Example 5 | | N-(Pyridin-3-yl)-[1-(2-chlorobenzyl)-indol-3-yl]glyoxylamide | | | | |
| Example 6 | | N-(4-Fluorophenyl)-[1-(4-fluorobenzyl)-indol-3-yl]glyoxylamide | | | | |
| Example 7 | | N-(4-Nitrophenyl)-[1-(4-fluorobenzyl)-indol-3-yl]glyoxylamide | | | | |
| Example 8 | | N-(2-Chloropyridin-3-yl)-[1-(4-fluoro-benzyl)indol-3-yl]glyoxylamide | | | | |
| Example 9 | | N-(Pyridin-4-yl)-(1-benzylindol-3-yl)-glyoxylamide | | | | |
| Example 10 | | N-(Pyridin-4-yl)-[1-(3-pyridylmethyl)-indol-3-yl]glyoxylamide | | | | |
| Example 11 | | N-(4-Fluorophenyl)-[1-(2-pyridylmethyl) indol-3-yl]glyoxylamide | | | | |
| Example 12 | | N-4(Fluorophenyl)-[1-(3-pyridylmethyl)-indol-3-yl]glyoxylamide | | | | |
| Example 13 | | N-(Pyridin-4-yl)-[1-(4-chlorobenzyl)-indol-3-yl]glyoxylamide | | | | |
| Example 14 | | N-(Pyridin-4-yl)-[1-(2-chlorobenzyl)-indol-3-yl]glyoxylamide | | | | |

-continued

Elemental analysis:

Example 15  N-(Pyridin-2-yl)-[1-4-fluorobenzyl)-indol-3-yl]glyoxylamide
Example 16  N-(Pyridin-4-yl)-[1-(2-pyridylmethyl)-indol-3-yl]glyoxylamide
Example 17  (4-Phenylpiperazin-1-yl)-[1-(4-fluorobenzyl)indol-3-yl]glyoxylamide
Example 18  N-(Pyridin-2-yl)-(1-benzylindol-3-yl)-glyoxylamide
Example 19  N-(Pyridin-4-yl)-[1-(4-fluorobenzyl)-6-ethoxycarbonylaminoindol-3-yl]-glyoxylamide
Example 20  N-(Pyridin-4-yl)-[1-(4-fluorobenzyl)-5-ethoxycarbonylaminoindol-3-yl]-glyoxylamide -continued Elemental analysis:

Example 21  N-(Pyridin-4-yl)-[1-(4-fluorobenzyl)-6-cyclopentyloxycarbonylaminoindol-3-yl]-glyoxylamide
Example 22  4-(Pyridin-4-yl)-piperazin-1-yl)-[1-(4-fluorobenzyl)indol-3-yl)-glyoxylamide.
Example 23  N-(3,4,5-Trimethoxybenzyl)-N-(allyl-aminocarbonyl-2-methylprop-1-yl)-[1-(4-fluorobenzyl)indol-3-yl]glyoxylamide
Example 24  N-(Pyridin-4-yl)-[1-(4-fluorobenzyl)-5-methoxyindol-3-yl]glyoxylamide
Example 25  N-(Pyridin-4-yl)-[1-(4-fluorobenzyl)-5-hydroxyindol-3-yl]glyoxylamide
Example 26  N-pyridin-4-yl-[1-(4-fluorobenzyl)-5-ethoxycarbonylaminomethylindol-3-yl]-glyoxylamide

TABLE 1

Novel indolylglyoxylamides according to reaction Scheme 1

Formula 1

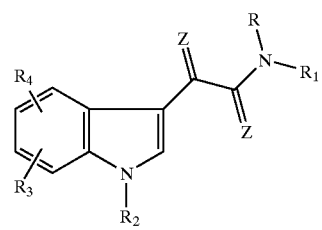

| Example | R | $R_1$ | $R_2$ | $R_3$ | $R_4$ | Z | M.p. |
|---|---|---|---|---|---|---|---|
| Ex. 1 | H | 4-pyridyl | —CH$_2$—(4-fluorophenyl) | H | H | O | 225–6° C. |
| Ex. 2 | H | 4-pyridyl | CH$_3$ | H | H | O | 176° C. |
| Ex. 3 | H | 3-pyridyl | —CH$_2$—(4-fluorophenyl) | H | H | O | 173° C. |
| Ex. 4 | H | 3-pyridyl | —CH$_2$—phenyl | H | H | O | 140° C. |
| Ex. 5 | H | 3-pyridyl | —CH$_2$—(2-chlorophenyl) | H | H | O | 185° C. |

TABLE 1-continued

Novel indolylglyoxylamides according to reaction Scheme 1

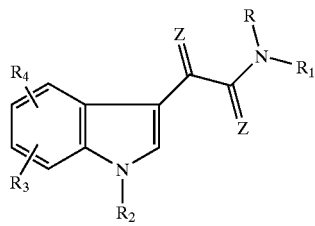

Formula 1

| Example | R | $R_1$ | $R_2$ | $R_3$ | $R_4$ | Z | M.p. |
|---|---|---|---|---|---|---|---|
| Ex. 6 | H | —⌬—F (4-F-phenyl) | —CH$_2$—⌬—F (4-F-benzyl) | H | H | O | 199° C. |
| Ex. 7 | H | —⌬—NO$_2$ (4-NO$_2$-phenyl) | —CH$_2$—⌬—F (4-F-benzyl) | H | H | O | >250° C. |
| Ex. 8 | H | 2-Cl-pyridin-3-yl | —CH$_2$—⌬—F (4-F-benzyl) | H | H | O | 149° C. |
| Ex. 9 | H | pyridin-4-yl | —CH$_2$—⌬ (benzyl) | H | H | O | 178–180° C. |
| Ex. 10 | H | pyridin-4-yl | —CH$_2$-pyridin-3-yl | H | H | O | 179° C. |
| Ex. 11 | H | 4-F-phenyl | —CH$_2$-pyridin-2-yl | H | H | O | 132° C. |
| Ex. 12 | H | 4-F-phenyl | pyridin-3-yl | H | H | O | 144° C. |
| Ex. 13 | H | pyridin-4-yl | —CH$_2$—⌬—Cl (4-Cl-benzyl) | H | H | O | 234° C. |
| Ex. 14 | H | pyridin-4-yl | —CH$_2$—⌬—Cl (2-Cl-benzyl) | H | H | O | 184° C. |
| Ex. 15 | H | pyridin-2-yl | —CH$_2$—⌬—F (4-F-benzyl) | H | H | O | 141° C. |

TABLE 1-continued

Novel indolylglyoxylamides according to reaction Scheme 1

Formula 1

| Example | R | R₁ | R₂ | R₃ | R₄ | Z | M.p. |
|---|---|---|---|---|---|---|---|
| Ex. 16 | H | 4-pyridyl | —CH₂-(2-pyridyl) | H | H | O | 202° C. |
| Ex. 17 | R + R₁ zusam. | piperidin-1-yl-phenyl | —CH₂-(4-F-phenyl) | H | H | O | 115° C. |
| Ex. 18 | H | 2-pyridyl | —CH₂-phenyl | H | H | O | 112–3° C. |
| Ex. 19 | H | 4-pyridyl | —CH₂-(4-F-phenyl) | 6-NHCOOEt | H | O | >250° C. |
| Ex. 20 | H | 4-pyridyl | —CH₂-(4-F-phenyl) | 6-NHCOOEt | H | O | 183° C. |
| Ex. 21 | H | 4-pyridyl | —CH₂-(4-F-phenyl) | 5-NHCOO-cyclopentyl | H | O | Olig |
| Ex. 22 | R + R₁ zusam. | 4-(piperidin-1-yl)-pyridyl | —CH₂-(4-F-phenyl) | H | H | O | 160–62° C. |
| Ex. 23 | —CH₂-(3,4,5-trimethoxyphenyl) | CH(CH₂CH₃)(CH(CH₃))C(O)NH-allyl | —CH₂-(4-F-phenyl) | H | H | O | 139–141° C. |
| Ex. 24 | H | 4-pyridyl | —CH₂-(4-F-phenyl) | 6-OCH₃ | H | O | 188° C. |
| Ex. 25 | H | 4-pyridyl | —CH₂-(4-F-phenyl) | 6-OH | H | O | >250° C. |

TABLE 1-continued

Novel indolylglyoxylamides according to reaction Scheme 1

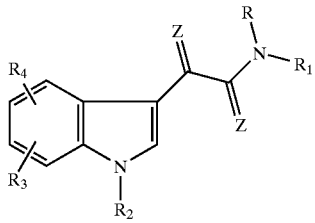

Formula 1

| Example | R | $R_1$ | $R_2$ | $R_3$ | $R_4$ | Z | M.p. |
|---|---|---|---|---|---|---|---|
| Ex. 26 | H | 4-pyridyl | —CH₂—(4-F-phenyl) | 6-CH₂-NHCOOEt | H | O | 175–176 °C. |

Starting Materials for the Compounds of the General Formula 1 Prepared According to Synthesis Scheme 1, which Come from Table 1

All precursors for the final synthesis stages of Examples 1 to 22 and 24 to 26 are commercially available.

Furthermore, the compounds of the general formula I are also obtainable according to the synthesis route of Scheme 2, shown by the synthesis of the compound Example 27:

Scheme 2

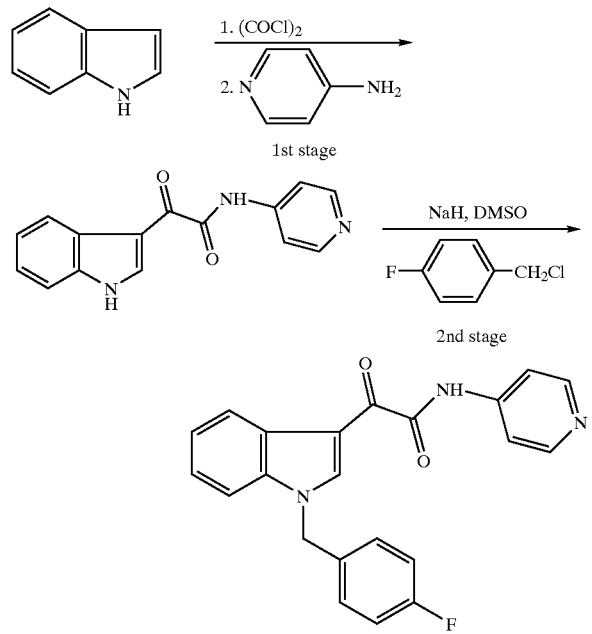

General Procedure for the Preparation of the Compounds of the General Formula 1 According to Scheme 2
1st Stage:

The indole derivative dissolved in a solvent, such as given above for oxalyl chloride, which can be unsubstituted or substituted on C-2 or in the phenyl ring, is added dropwise at a temperature between −5° C. and +5° C. to a solution of a simply molar up to 60% excess amount of oxalyl chloride prepared under a nitrogen atmosphere in an aprotic or nonpolar solvent, such as, for example, in diethyl ether, methyl tert-butyl ether, tetrahydrofuran, dioxane or alternatively dichloromethane. The reaction solution is then heated for 1 to 5 hours to a temperature between 10° C. and 120° C., preferably between 20° C. and 80° C., particularly between 30° C. and 60° C., and the solvent is then evaporated. The residue of the (indol-3-yl)glyoxylic acid chloride which remains is dissolved or suspended in an aprotic solvent, such as, for example, tetrahydrofuran, dioxane, diethyl ether, toluene or alternatively in a dipolar aprotic solvent, such as, for example, dimethylformamide, dimethylacetamide or dimethyl sulfoxide, cooled to a temperature between −10° C. and +10° C., preferably to −5° C. to 0° C., and treated with a solution of the primary or secondary amine in a diluent in the presence of an acid scavenger. Possible diluents are the solvents used for the dissolution of the "indolyl-3-glyoxylic acid chloride". Acid scavengers used are triethylamine, pyridin, dimethylaminopyridine, basic ion exchanger, sodium carbonate, potassium carbonate, powdered potassium hydroxide and excess primary or secondary amine employed for the reaction. The reaction takes place at a temperature from 0° C. to 120° C., preferably at 20–80° C., particularly between 40° C. and 60° C. After a reaction time of 1–4 hours and standing at room temperature for 24 hours, the precipitate is digested with water, and the solid is filtered off with suction and dried in vacuo. The desired compound is purified by recrystallization in an organic solvent or by column chromatography on silica gel or alumina. The solvent used is, for example, a mixture of dichloromethane and ethanol (10:1, vol/vol).

2nd Stage

The "indol-3-ylglyoxylamide" obtained according to the abovementioned 1st Stage procedure is dissolved in a protic, dipolar aprotic or nonpolar organic solvent, such as, for example, in isopropanol, tetrahydrofuran, dimethyl sulfoxide, dimethylformamide, dimethyl-acetamide, N-methylpyrrolidone, dioxane, toluene or methylene chloride and added dropwise to a suspension of a base such as, for example, sodium hydride, powdered potassium hydroxide, potassium tert-butoxide, dimethylaminopyridine or sodium amide in a suitable solvent, in a molar amount or in excess prepared in a 3-necked flask under an $N_2$ atmosphere. The desired alkyl, aralkyl or heteroaralkyl halide is then added either in undiluted form or in a diluent which was also used, for example, to dissolve the "indol-3-yl glyoxylamide", if appropriate with addition of a catalyst, such as, for example, copper, and the mixture is allowed to react for some time, e.g. 30 minutes to 12 hours, and the temperature is kept within a range between 0° C. and 120° C., preferably between 30° C. and 80° C., particularly between 50 and 70° C. After completion of the reaction, the reaction mixture is added to water, the solution is extracted, for example, with diethyl ether, dichloromethane, chloroform, methyl tert-butyl ether, tetrahydrofuran or N-butanol and the organic phase obtained in each case is dried using anhydrous sodium sulfate.

The organic phase is concentrated in vacuo, the residue which remains is crystallized by trituration or the oily residue is purified by distillation or by column chromatography or flash chromatography on silica gel or alumina. The eluent used is, for example, a mixture of methylene chloride and diethyl ether in the ratio 8:2 (vol/vol) or a mixture of methylene chloride and ethanol in the ratio 9:1 (v/v).

WORKING EXAMPLES

According to this general procedure for Stages 1 and 2, on which synthesis Scheme 2 is based, compounds were synthesized which have already been prepared according to the synthesis course of reaction Scheme 1 and are evident from Table 1. The relevant precursors of these compounds are evident from Table 2.

Example 27

N-(pyridin-4-yl)-[1-(4-flurobenzyl)indol-3-yl]-glyoxylamide (Final Substance, Identical to Example 1)

1st Stage

N-(Pyridin-4-yl)-(indol-3-yl)glyoxylamide

A solution of 10 g (85.3 mmol) of indole in 100 ml of ether is added dropwise at 0° C. to a solution of 9 ml of oxalyl chloride in 100 ml of anhydrous ether. The mixture is kept under reflux for 3 hours. A suspension of 12 g (127.9 mmol) of 4-aminopyridine in 500 ml of tetrahydrofuran is then added dropwise at −5° C., and the reaction mixture is heated to reflux temperature with stirring for 3 hours and allowed to stand overnight at room temperature. The precipitate is filtered and treated with water and the dried compound is purified on a silica gel column (silica gel 60, Merck AG, Darmstadt) using the eluent methylene chloride/ethanol (10:1, v/v).

Yield: 9.8 g (43.3% of theory) M.p.: from 250° C.

2nd stage

N-(Pyridin-4-yl)-[1-[4-fluorobenzylindol-3-yl] glyoxylamide

The N-(pyridin-4-yl)-(indol-3-yl)glyoxylamide obtained according to the 1st stage is reacted with 4-fluorobenzyl chloride according to the "benzylation procedure" (Page 11) and the compound obtained is isolated.

Yield: 41% of theory
M.p.: 224–225° C.

| Elemental analysis: | | | |
|---|---|---|---|
| Calc. | C 70.77 | H 4.32 | N 11.25 |
| Found | C 70.98 | H 4.40 | N 11.49 |
| Example 28 | N-(4-Nitrophenyl)-[1-(4-fluorobenzyl)-indol-3-yl]glyoxylamide (Final substance, identical to Example 7) | | |
| Example 29 | N-(4-Fluorophenyl)-[1-(4-fluorobenzyl)-indol-3-yl]glyoxylamide (Final substance, identical to Example 6) | | |
| Example 30 | N-)Pyridin-3-yl)-[1-(4-fluorobenzyl)-indol-3-yl]glyoxylamide (Final substance, identical to Example 3) | | |

The following precursors (1st stage of reaction scheme 2, Table 2) were obtained according to the present Scheme 2.

| Example 31 | N-(Pyridin-4-yl)-(indol-3-yl)-glyoxylamide |
|---|---|
| Example 32 | N-(4-Nitrophenyl)-(indol-3-yl)-glyoxylamide |
| Example 33 | N-(4-Fluorophenyl)-(indol-3-yl)-glyoxlyamide |
| Example 34 | N-(Pyridin-3-yl)-(indol-3-yl)-glyoxylamide |

TABLE 2

Novel indolylglyoxylamides according to reaction Scheme 2

Formula 1

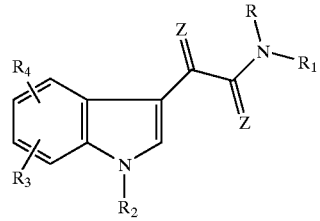

| Example | R | $R_1$ | $R_2$ | $R_3$ | $R_4$ | Z | M.p. |
|---|---|---|---|---|---|---|---|
| Ex. 31 | H | 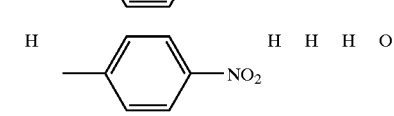 | H | H | H | O | >250° C. |
| Ex. 32 | H | 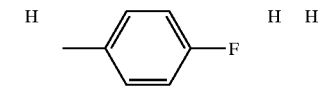—NO$_2$ | H | H | H | O | >250° C. |
| Ex. 33 | H | 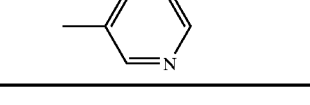—F | H | H | H | O | 233–5° C. |
| Ex. 34 | H | | H | H | H | O | >235° C. |

What is claimed is:

1. A method of treating asthma and/or allergic reaction in a mammal comprising the step of administering to said mammal a treatment-effective amount of an N-substituted indol-3-glyoxylamide of formula I:

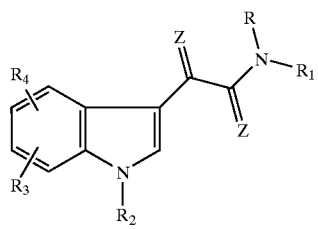

or an acid addition salt thereof; wherein the radicals R, $R_1$, $R_2$, $R_3$, R4 and Z have the following meanings:

R represents
(1) hydrogen, or
(2) ($C_1$–$C_6$)-alkyl, wherein the alkyl group is optionally mono- or polysubstituted by a phenyl ring, which ring is optionally mono- or polysubstituted by halogen, ($C_1$–$C_6$)-alkyl, ($C_3$–$C_7$)-cycloalkyl, carboxyl groups, carboxyl groups esterified with ($C_1$–$C_6$)-alkanols, trifluoromethyl groups, hydroxly groups, methoxy groups, ethoxy groups, benzyloxy groups and benzyl groups which are optionally mono- or polysubstituted on the phenyl moiety by ($C_1$–$C_6$)-alkyl groups, halogen atoms or trifluoromethyl groups;

$R_1$ represents
(1) a phenyl ring which is mono- or polysubstituted by ($C_1$–$C_6$)-alkyl, ($C_1$–$C_6$)-alkoxy, hydroxyl, benzyloxy, intro, amino, ($C_1$–$C_6$)-alkylamino, ($C_1$–$C_6$)-alkoxycarbonylamino and by a carboxyl group or a carboxyl group esterified by a ($C_1$–$C_6$)-alkanol;
(2) a 2- or 4-pyrimidinyl-heterocycle or a pyridylmethyl radical in which $CH_2$ is in the 2-, 3- or 4-position, wherein the 2-pyrimidinyl ring is optionally mono- or polysubstituted by a methyl group;
(3) a 2-, 3- or 4-quinolyl structure substituted by ($C_1$–$C_6$)-alkyl, halogen) a nitro group, an amino group or a ($C_1$–$C_6$)-alkylamino radical;
(4) a 2-, 3- or 4-quinolyl methyl group wherein the ring carbons of the pyridylmethyl and quinolylmethyl radicals are optionally substituted by ($C_1$–$C_6$)-alkyl, ($C_1$–$C_6$)-alkoxy, nitro, amino and ($C_1$–$C_6$)-alkoxycarbonylamino;
(5) if R represents hydrogen or a benzyl group, $R_1$ can represent the acid radical of a natural amino acid, or sarcosine wherein the amino group of said natural amino acid or sarcosine is present in protected or unprotected form wherein if $R_1$ represents an asparagyl or a glutamyl radical having a second non-bonded carboxyl group, said non-bonded carboxyl group is present as a free carboxyl group or in the form of an ester with ($C_1$–$C_6$-alkanols;
(6) an allylaminocarbonyl-2-methylprop-1-yl group; or $R_1$ and R, together with the nitrogen atom to which they are bonded, form a piperazine ring of formula III:

Formula III

or a homopiperazine ring if $R_1$ represents an aminoalkylene group, in which $R_7$ represents an alkyl radical, a phenyl ring which is optionally mono- or polysubstituted by ($C_1$–$C_6$-alkyl, ($C_1$–$C_6$)-alkoxy, halogen, a intro group, an amino function, ($C_1$–$C_6$)-alkylamino, benzhydryl group or bis-p-fluorobenzylhydryl group;

$R_2$ represents
(1) hydrogen;
(2) a ($C_1$–$C_6$)-alkyl group, said alkyl group being optionally mono- or polysubstituted by halogen or a phenyl ring, which ring is optionally mono- or polysubstituted by halogen, ($C_1$–$C_6$)-alkyl, ($C_3$–$C_7$)-cycloalkyl, carboxyl groups, carboxyl groups esterified with ($C_1$–$C_6$)-alkanols, trifluoromethyl groups, hydroxyl groups, methoxy groups, ethoxy groups, or benzyloxy groups;
or by a 2-quinolyl group or a 2-,3- or 4-pyridyl structure which are optionally mono- or polysubstituted by halogen, ($C_1$–$C_4$)-alkyl groups or ($C_1$–$C_4$)-alkoxy groups;
(3) an aroyl radical, wherein the aroyl moiety on which the radical is based is a phenyl ring which is optionally mono- or polysubstituted by halogen, ($C_1$–$C_6$)-alkyl, ($C_3$–$C_7$)-cycloalkyl, carboxyl groups, carboxyl groups esterified with ($C_1$–$C_6$)-alkanols, trifluoromethyl groups, hydroxyl groups, methoxy groups, ethoxy groups, or benzyloxy groups;

$R_3$ and $R_4$, which are identical or different, represent hydrogen, hydroxyl, ($C_1$–$C_6$)-alkyl, ($C_3$–$C_7$)-cycloalkyl, ($C_1$–$C_6$)-alkanoyl, ($C_1$–$C_6$)-alkoxy, halogen, benzoxy, a nitro group, an amino group, a ($C_1$–$C_6$-mono- or dialkyl substituted amino group, a ($C_1$–$C_6$)-alkoxycarbonylamino function or a ($C_1$–$C_3$)-alkoxycarbonylamino- ($C_1$–$C_3$)-alkyl function; and Z represents O;
wherein alkyl, alkanol, alkoxy and alkylamino groups may be straight chained or branched.

2. A method of treating asthma and/or allergic reaction in a mammal comprising administering to said mammal a treatment-effective amount of an N-substituted indol-3-glyoxylamide of claim 1, wherein R is hydrogen or a benzyl group and $R_1$ is the acid radical of an amino acid selected from the group consisting of α-glycyl, α-alanyl, α-leucyl, α-isoleucyl, α-seryl, α-phenylalanyl, α-histidyl, α-prolyl, α-arginyl, α-lysyl, α-asparagyl and α-glutamyl.

3. A method of treating asthma and/or allergic reaction in a mammal comprising administering to said mammal a treatment-effective amount of an N-substituted indol-3-glyoxylamide of claim 2, wherein R represents hydrogen or a benzyl group and $R_1$ represents α-asparagyl or α-glutamyl in which the non-bonded carboxyl group is a methyl, ethyl or tert-butyl ester.

4. A method of treating asthma and/or allergic reaction in a mammal comprising administering to said mammal a treatment-effective amount of an N-substituted indo-3-glyoxylamide of claim 2, wherein R represents hydrogen or a benzyl group and $R_1$ represents the acid radical of a natural amino acid protected by a carbobenzoxy radical, a tert-butoxycarbonyl radical or an acetyl group.

5. A method of treating asthma and/or allergic reaction in a mammal comprising administering to said mammal a treatment-effective amount of an N-substituted indol-3-glyoxylamide of formula I:

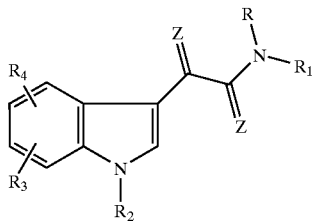

or an acid addition salt thereof, wherein the radicals R, $R_1$, $R_2$, $R_3$, $R_4$ and Z have the following meanings:

R represents
(1) hydrogen, or
(2) $(C_1-C_6)$-alkyl, wherein the alkyl group is optionally mono- or polysubstituted by a phenyl ring, which ring is optionally mono- or polysubstituted by halogen, $(C_1-C_6)$-alkyl, $(C_3-C_7)$-cycloalkyl, carboxyl groups, carboxyl groups esterified with $(C_1-C_6)$-alkanols, trifluoromethyl group; hydroxyl groups methoxy groups, ethoxy groups, benzyloxy groups and benzyl groups which are optionally mono- or polysubstituted on the phenyl moiety by $(C_1-C_6)$-alkyl groups, halogen atoms or trifluoromethyl groups;

$R_1$ represents
(1) a phenyl ring which is mono- or polysubstituted by $(C_1-C_6)$-alkyl, $(C_1-C_6)$-alkoxy, hydroxyl, benzyloxy, nitro, amino, $(C_1-C_6)$-alkylamino, $(C_1-C_6)$-alkoxycarbonylamino and by a carboxyl group or a carboxyl group esterified by a $(C_1-C_6)$-alkanol;
(2) a 2- or 4-pyrimidinyl-heterocycle or a pyridylmethyl radical in which $CH_2$ is in the 2-, 3- or 4-position, wherein the 2-pyrimidinyl ring is optionally mono- or polysubstituted by a methyl group;
(3) a 2-, 3- or 4-quinolyl structure substituted by $(C_1-C_6)$-alkyl, halogen, a nitro group, an amino group or a $(C_1-C_6)$-alkylamino radical;
(4) a 2-, 3- or 4-quinolyl methyl group, wherein the ring carbons of the pyridylmethyl and quinolylmethyl radicals are optionally substituted by $(C_1-C_6)$-alkyl, $(C_1-C_6)$-alkoxy, nitro, amino and $(C_1-C_6)$-alkoxycarbonylamino;
(5) if R represents hydrogen or a benzyl group, $R_1$ can represent the acid radical of a natural amino acid, or sarcosine wherein the amino group of said natural amino acid or sarcosine is present in protected or unprotected form wherein if $R_1$ represents an asparagyl or a glutamyl radical having a second non-bonded carboxyl group, said non-bonded carboxyl group is present as a free carboxyl group or in the form of an ester with $(C_1-C_6)$-alkanols;
(6) an allylaminocarbonyl-2-methylprop-1-yl group; or
$R_1$ and R, together with the nitrogen atom to which they are bonded, form a piperazine ring of formula III:

Formula III or a homopiperazine ring if $R_1$ represents an aminoalkylene group, in which $R_7$ represents an alkyl radical, a phenyl ring which is optionally mono- or polysubstituted by $(C_1-C_6)$-alkyl, $(C_1-C_6)$-alkoxy, halogen, a nitro group, an amino function, $(C_1-C_6)$-alkylamino, benzhydryl group or bis-p-fluorobenzylhydryl group;

$R_2$ represents
(1) hydrogen;
(2) a $(C_1-C_6)$-alkyl group, said alkyl group being optionally mono- or polysubstituted by halogen or a phenyl ring, which ring is optionally mono- or polysubstituted by halogen, $(C_1-C_6)$-alkyl, $(C_3-C_7)$-cycloalkyl, carboxyl groups, carboxyl groups esterified with $(C_1-C_6)$-alkanols, trifluoromethyl groups, hydroxyl groups, methoxy groups, ethoxy groups, or benzyloxy groups;
or by a 2-quinolyl group or a 2-,3- or 4-pyridyl structure which are optionally mono- or polysubstituted by halogen, $(C_1-C_4)$-alkyl groups or $(C_1-C_4)$-alkoxy groups;
(3) an aroyl radical, wherein the aroyl moiety on which the radical is based is a phenyl ring which is optionally mono- or polysubstituted by halogen, $(C_1-C_6)$-alkyl, $(C_3-C_7)$-cycloalkyl, carboxyl groups, carboxyl groups esterified with $(C_1-C_6)$-alkanols, trifluoromethyl groups, hydroxyl groups, methoxy groups, ethoxy groups, or benzyloxy groups;

$R_3$ and $R_4$, which are identical or different, represent hydrogen, hydroxyl, $(C_1-C_6)$-alkyl, $(C_3-C_7)$-cycloalkyl, $(C_1-C_6)$-alkanoyl, $(C_1-C_6)$-alkoxy, halogen, benzoxy, a nitro group, an amino group, a $(C_1-C_4)$-mono- or dialkyl substituted amino group, a $(C_1-C_3)$-alkoxy-carbonylamino function or a $(C_1-C_3)$-alkoxy-carbonylamino- $(C_1-C_3)$-alkyl function; and Z represents O
wherein alkyl, alkanol alkoxy and alkylamino groups may be straight chained or branched, and
wherein R, $R_1$, $R_2$, $R_3$, $R_4$ and Z are selected such that the glyoxylamide is a member selected from the group consisting of 4-Phenylpiperazin-1-yl)-[1-(4-fluorobenzyl)indol-3-yl]-glyoxylamide; and 4-(Pyridin-4-yl)-piperazin-1-yl)-[(1-(4-fluorobenzyl)indol-3-yl]-glyoxylamide.

6. A method of suppressing an immunological reaction and/or inducing regression of an immunological reaction in a mammal comprising administering to said mammal a treatment-effective amount of an N-substituted indol-3-glyoxylamide of formula I;

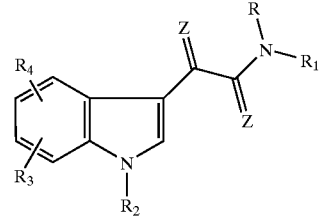

or an acid addition salt thereof, wherein the radicals R, $R_1$, $R_2$, $R_3$, $R_4$ and Z have the following meanings:

R represents
(1) hydrogen, or
(2) $(C_1-C_6)$-alkyl, wherein the alkyl group is optionally mono- or polysubstituted by a phenyl ring, which ring is optionally mono- or polysubstituted by halogen, $(C_1-C_6)$-alkyl, $(C_3-C_7)$-cycloalkyl, carboxyl groups, carboxyl groups esterified with $(C_1-C_6)$-alkanols, trifluoromethyl groups, hydroxyl groups, methoxy groups, ethoxy groups, benzyloxy groups and benzyl groups which are optionally mono- or polysubstituted on the phenyl moiety by $(C_1-C_6)$-alkyl groups, halogen atoms or trifluoromethyl groups;

$R_1$ represents
(1) a phenyl ring which is mono- or polysubstituted by $(C_1-C_6)$-alkyl, $(C_1-C_6)$-alkoxy, hydroxyl, benzyloxy, nitro, amino, $(C_1-C_6)$-alkylamino, $(C_1-C_6)$-alkoxycarbonylamino and by a carboxyl group or a carboxyl group esterified by a $(C_1-C_6)$-alkanol;
(2) 2- or 4-pyrimidinyl-heterocycle or a pyridylmethyl radical in which $CH_2$ is in the 2-, 3- or 4-position, wherein the 2-pyrimidinyl ring is optionally mono- or polysubstituted by a methyl group;
(3) a 2-, 3- or 4-quinolyl structure substituted by $(C_1-C_6)$-alkyl, halogen, a nitro group, an amino group or a $(C_1-C_6)$-alkylamino radical;
(4) a 2-, 3- or 4-quinolyl methyl group, wherein the ring carbons of the pyridylmethyl and quinolylmethyl radicals are optionally substituted by $(C_1-C_6)$-alkyl, $(C_1-C_6)$-alkoxy. nitro, amino and $(C_1-C_6)$-alkoxycarbonylamino;
(5) if R represents hydrogen or a benzyl group, $R_1$ can represent the acid radical of a natural amino acid, or sarcosine wherein the amino group of said natural amino acid or sarcosine is present in protected or unprotected form wherein if $R_1$ represents an asparagyl or a glutamyl radical having a second non-bonded carboxyl group, said non-bonded carboxyl group is present as a free carboxyl group or in the form of an ester with $(C_1-C_6)$-alkanols;
(6) an allylaminocarbonyl-2-methylprop-1-yl group; or $R_1$ and R, together with the nitrogen atom to which they are bonded, form a piperazine ring of formula III:

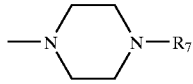

Formula III or a homopiperazine ring if $R_1$ represents an aminoalkylene group, in which $R_7$ represents an alkyl radical, a phenyl ring which is optionally mono- or polysubstituted by $(C_1-C_6)$-alkyl, $(C_1-C_6)$-alkoxy, halogen, a nitro group, an amino function, $(C_1-C_6)$-alkylamino, benzhydryl group or bis-p-fluorobenzylhydryl group;

$R_2$ represents
(1) hydrogen;
(2) a $(C_1-C_6)$-alkyl group,
said alkyl group being optionally mono- or polysubstituted by halogen or a phenyl ring,
which ring is optionally mono- or polysubstituted by halogen, $(C_1-C_6)$-alkyl, $(C_2-C_7)$-cycloalkyl, carboxyl groups, carboxyl groups esterified with $(C_1-C_6)$-alkanols, trifluoromethyl groups, hydroxyl groups, methoxy groups, ethoxy groups, or benzyloxy groups;
or by a 2-quinolyl group or a 2-,3- or 4-pyridyl structure
which are optionally mono- or polysubstituted by halogen, $(C_1-C_4)$-alkyl groups or $(C_1-C_4)$-alkoxy groups;
(3) an aroyl radical, wherein the aroyl moiety on which the radical is based is a phenyl ring which is optionally mono- or polysubstituted by halogen, $(C_1-C_6$-alkyl, $(C_3-C_7)$-cycloalkyl, carboxyl groups, carboxyl groups esterified with $(C_1-C_6)$-alkanols, trifluoromethyl groups, hydroxyl groups, methoxy groups, ethoxy groups, or benzyloxy groups;

$R_3$ and $R_4$, which are identical or different, represent hydrogen, hydroxyl, $(C_1-C_6)$-alkyl, $(C_3-C_7)$-cycloalkyl, $(C_1-C_6)$-alkanoyl, $(C_1-C_6)$-alkoxy, halogen, benzoxy, a nitro group, an amino group, a $(C_1-C_4)$-mono- or dialkyl substituted amino group, a $(C_1-C_3)$-alkoxycarbonylamino function or a $(C_1-C_3)$-alkoxycarbonylamino-$(C_1-C_3)$-alkyl function; and Z represents O wherein alkyl, alkanol, alkoxy and alkylamino groups may be straight chained or branched.

7. A method of suppressing and/or inducing regression of an immunological reaction in a mammal comprising administering to said mammal a treatment-effective amount of an N-substituted indol-3-glyoxylamide of claim 6, wherein R is hydrogen or a benzyl group and $R_1$ is the acid radical of an amino acid selected from the group consisting of α-glycyl, α-alanyl, α-leucyl, α-isoleucyl, α-seryl, α-phenylalanyl, α-histidyl, αprolyl, α-arginyl, α-lysyl, α-asparagyl and α-glutamyl.

8. A method of suppressing and/or inducing regression of an immunological reaction in a mammal comprising administering to said mammal a treatment-effective amount of an N-substituted indol-3-glyoxylamide of claim 7, wherein R represents hydrogen or a benzyl group and $R_1$ represents α-asparagyl or α-glutamyl, in which the non-bonded carboxyl group is a methyl, ethyl or tert-butyl ester.

9. A method of suppressing and/or inducing regression of an immunological reaction in a mammal comprising administering to said mammal a treatment-effective amount of an N-substituted indol-3-glyoxylamide of claim 7, wherein R represents hydrogen or a benzyl group and $R_3$ represents the acid radical of a natural amino acid protected by a carbobenzoxy radical, a tert-butoxycarbonyl radical or an acetyl group.

10. A method of suppressing and/or inducing regression of an immunological reaction in a mammal comprising the step of administering to said mammal a treatment-effective amount of an N-substituted indol-3-glyoxylamide of formula I:

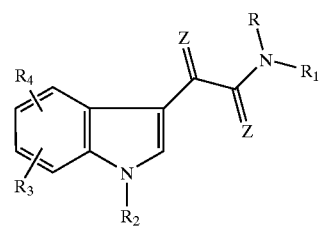

I or an acid addition salt thereof; wherein the radicals R, $R_1$, $R_2$, $R_3$, $R_4$ and Z have the following meanings:

R represents
(1) hydrogen, or
(2) $(C_1-C_6)$-alkyl, wherein the alkyl group is optionally mono- or polysubstituted by a phenyl ring,
which ring is optionally mono- or polysubstituted by halogen, $(C_1-C_6)$-alkyl, $(C_3-C_7)$-cycloalkyl, carboxyl groups, carboxyl groups esterified with $(C_1-C_6)$-alkanols, trifluoromethyl groups, hydroxyl groups, methoxy groups, ethoxy groups, benzyloxy groups and benzyl groups which are optionally mono- or polysubstituted on the phenyl moiety by (C$_1$–C$_6$-alkyl groups, halogen atoms or trifluoromethyl groups;

R$_1$, represents (1) a phenyl ring which is mono- or polysubstituted by (C$_1$–C$_6$)-alkyl, (C$_1$–C$_6$)-alkoxy, hydroxyl, benzyloxy, nitro, amino, (C$_1$–C$_6$-alkylamino, (C$_1$–C$_6$)-alkoxycarbonylamino and by a carboxyl group or a carboxyl group esterified by a (C$_1$–C$_6$)-alkanol;

(2) a 2- or 4-pyrimidinyl-heterocycle or a pyridylmethyl radical in which CH$_2$ is in the 2-, 3- or 4-position, wherein the 2-pyrimidinyl ring is optionally mono- or polysubstituted by a methyl group;

(3) a 2-, 3- or 4-quinolyl structure substituted by (C$_1$–C$_6$)-alkyl, halogen, a nitro group, an amino group or a (C$_1$–C$_6$)-alkylamino radical;

(4) a 2-, 3- or 4-quinolyl methyl group, wherein the ring carbons of the pyridylmethyl and quinolylmethyl radicals are optionally substituted by (C$_1$–C$_6$)-alkyl, (C$_1$–C$_6$)-alkoxy, nitro, amino and (C$_1$–C$_6$)-alkoxycarbonylamino;

(5) if R represents hydrogen or a benzyl group, R$_1$ can represent the acid radical of a natural amino acid, or sarcosine wherein the amino group of said natural amino acid or sarcosine is present in protected or unprotected form wherein if R$_1$ represents an asparagyl or a glutamyl radical having a second non-bonded carboxyl group, said non-bonded carboxyl group is present as a free carboxyl group or in the form of an ester with (C$_1$–C$_6$)-alkanols;

(6) an allylaminocarbonyl-2-methylprop-1-yl group; or

R$_1$ and R, together with the nitrogen atom to which they are bonded, form a piperazine ring of formula III:

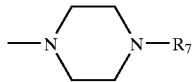

Formula III or a homopiperazine ring if R$_1$ represents an aminoalkylene group, in which R$_7$ represents an alkyl radical, a phenyl ring which is optionally mono- or polysubstituted by (C$_1$–C$_6$)-alkyl, (C$_1$–C$_6$)-alkoxy, halogen, a nitro group, an amino function, (C$_1$–C$_6$)-alkylamino, benzhydryl group or bis-p-fluorobenzylhydryl group;

R$_2$ represents (1) hydrogen;

(2) a (C$_1$–C$_6$)-alkyl group,
said alkyl group being optionally mono- or polysubstituted by halogen or a phenyl ring,
which ring is optionally mono- or polysubstituted by halogen, (C$_1$–C$_6$)-alkyl, (C$_1$–C$_7$)-cycloalkyl, carboxyl groups, carboxyl groups esterified with (C$_1$–C$_6$)-alkanols, trifluoromethyl groups, hydroxyl groups, methoxy groups, ethoxy groups, or benzyloxy groups;
or by a 2-quinolyl group or a 2-,3- or 4-pyridyl structure
which are optionally mono- or polysubstituted by halogen, (C$_1$–C$_4$)-alkyl groups or (C$_1$–C$_4$)-alkoxy groups;

(3) an aroyl radical, wherein the aroyl moiety on which the radical is based is a phenyl ring which is optionally mono- or polysubstituted by halogen, (C$_1$–C$_6$)-alkyl, (C$_3$–C$_7$)-cycloalkyl, carboxyl groups, carboxyl groups esterified with (C$_1$–C$_6$)-alkanols, trifluoromethyl groups, hydroxyl groups, methoxy groups, ethoxy groups, or benzyloxy groups;

R$_3$ and R$_4$, which are identical or different, represent hydrogen, hydroxyl (C$_1$–C$_6$)-alkyl, (C$_3$–C$_7$)-cycloalkyl, (C$_1$–C$_6$)-alkanoyl, (C$_1$–C$_6$)-alkoxy halogen, benzoxy, a nitro group, an amino group, a (C$_1$–C$_4$)-mono- or dialkyl substituted amino group, a (C$_1$–C$_3$)-alkoxy-carbonylamino function or a (C$_1$–C$_3$)-alkoxy-carbonylamino-(C$_1$–C$_3$)-alkyl function; and Z represents O wherein alkyl, alkanol, alkoxy and alkylamino groups may be straight chained or branched, and Wherein R, R$_1$, R$_2$, R$_3$, R$_4$ and Z are selected such that the glyoxylamide is a member selected from the group consisting of (4-Phenylpiperazin-1-yl)-[1-(4-fluorobenzyl)indol-3-yl]-glyoxylamide; and 4-(Pyridin-4-yl)-piperazin-1-yl)-[1-(4-fluorobenzyl)indol-3-yl]-glyoxylamide.

* * * * *

UNITED STATES PATENT AND TRADEMARK OFFICE
CERTIFICATE OF CORRECTION

PATENT NO. : 6,919,344 B2
APPLICATION NO. : 10/402931
DATED : July 19, 2005
INVENTOR(S) : Lebaut et al.

It is certified that error appears in the above-identified patent and that said Letters Patent is hereby corrected as shown below:

In the Claims:

In Claim 1, column 19, line 15, please replace "$R_2$, $R_3$, R4" with --$R_2$, $R_3$, $R_4$--;

In Claim 1, column 19, line 32, please replace "intro," with --nitro--;

In Claim 1, column 19, line 40, please replace "alkyl, halogen)" with --alkyl, halogen,--;

In Claim 1, column 19, line 55, please replace "($C_1$-$C_6$-alkanols;" with --($C_1$-$C_6$)-alkanols;--;

In Claim 1, column 20, line 1, please replace "($C_1$-$C_6$-" with -- ($C_1$-$C_6$)- --;

In Claim 1, column 20, line 2, please replace "intro" with --nitro--;

In Claim 1, column 20, line 35, please replace "($C_1$-$C_6$-mono-" with -- ($C_1$-$C_4$)-mono- --;

In Claim 1, column 20, line 36, please replace "($C_1$-$C_6$)-alkoxycarbonylamino" with --($C_1$-$C_3$)-alkoxycarbonylamino--;

In Claim 3, column 20, line 54, please replace "α-glutamyl" with --α-glutamyl,--;

In Claim 4, column 20, line 59, please replace "indo-3-" with -- indol-3- --;

In Claim 5, column 21, line 22, please replace "trifluoromethyl group, hydroxly groups meth-" with -- trifluoromethyl groups, hydroxly groups, meth- --;

In Claim 5, column 22, line 6, please replace "($C_1$-$C_6$-alkyl" with --($C_1$-$C_6$)-alkyl--;

In Claim 5, column 22, line 10, please replace "($C_1$-$C_6$-alkyl," with --($C_1$-$C_6$)-alkyl,--;

In Claim 5, column 22, line 39, please replace "4-Phenylpiperazin-1-yl)-[1-(4-" with -- (4-Phenylpiperazin-1-yl)-[1-(4- --;

In Claim 6, column 23, line 56, please replace "($C_2$-$C_7$)-cycloalkyl," with --($C_3$-$C_7$)-cycloalkyl,--;

UNITED STATES PATENT AND TRADEMARK OFFICE
CERTIFICATE OF CORRECTION

PATENT NO. : 6,919,344 B2
APPLICATION NO. : 10/402931
DATED : July 19, 2005
INVENTOR(S) : Lebaut et al.

It is certified that error appears in the above-identified patent and that said Letters Patent is hereby corrected as shown below:

In Claim 6, column 24, line 1, please replace "($C_1$-$C_6$-alkyl," with --($C_1$-$C_6$)-alkyl,--;

In Claim 6, column 24, line 2, please replace "($C_3$-$C_7$-cycloalkyl," with --($C_3$-$C_7$)-cycloalkyl,--;

In Claim 7, column 24, line 24, please replace "αprolyl," with --α-prolyl,--;

In Claim 8, column 24, line 37, please replace "$R_3$ represents" with --$R_1$ represents--;

In Claim 10, column 25, line 3, please replace "($C_1$-$C_6$-alkyl" with --($C_1$-$C_6$)-alkyl--;

In Claim 10, column 25, line 5, please replace "$R_1$, represents" with --$R_1$ represents--;

In Claim 10, column 25, line 8, please replace "($C_1$-$C_6$-alkylamino," with --($C_1$-$C_6$)-alkylamino,--;

In Claim 10, column 26, line 10, please replace "($C_1$-$C_7$)-cycloalkyl," with --($C_3$-$C_7$)-cycloalkyl,--.

Signed and Sealed this

Twenty-ninth Day of April, 2008

JON W. DUDAS
*Director of the United States Patent and Trademark Office*